United States Patent [19]

Mathur

[11] Patent Number: 5,439,967

[45] Date of Patent: * Aug. 8, 1995

[54] PROPYLENE GLYCOL STEARATE VESICLES

[75] Inventor: Rajiv Mathur, Sewell, N.J.

[73] Assignee: Micro Vesicular Systems, Inc., Nashua, N.H.

[*] Notice: The portion of the term of this patent subsequent to Nov. 9, 2010 has been disclaimed.

[21] Appl. No.: 148,952

[22] Filed: Nov. 8, 1993

Related U.S. Application Data

[63] Continuation-in-part of Ser. No. 761,253, Sep. 17, 1991, Pat. No. 5,260,065.

[51] Int. Cl.$^6$ ............................................. A61K 9/127
[52] U.S. Cl. ................... 424/450; 428/402.2
[58] Field of Search ............... 424/450; 428/402.2, 428/417; 436/829

[56] References Cited

U.S. PATENT DOCUMENTS

| | | | |
|---|---|---|---|
| 3,069,370 | 12/1962 | Jensen et al. | 260/23 |
| 3,372,201 | 5/1968 | Leary et al. | 260/615 |
| 3,957,971 | 5/1976 | Oleniacz | 424/70 |
| 4,075,131 | 2/1978 | Sterling | 252/542 |
| 4,182,330 | 10/1980 | Michaels | 128/260 |
| 4,235,871 | 11/1980 | Papahadjopoulos et al. | 424/19 |
| 4,241,046 | 12/1980 | Papahadjopoulos | 424/19 |
| 4,247,411 | 1/1981 | Vanlerberghe et al. | 252/316 |
| 4,271,344 | 8/1981 | Vanlerberghe et al. | 424/60 |
| 4,348,329 | 9/1982 | Chapman | 268/483 |
| 4,356,167 | 10/1982 | Kelly | 424/38 |
| 4,377,567 | 3/1983 | Geno | 424/1 |
| 4,399,313 | 8/1983 | Vanlerberghe et al. | 568/622 |
| 4,465,860 | 8/1984 | Vanlerberghe et al. | 568/36 |
| 4,536,324 | 8/1985 | Fujiwara | 252/311 |
| 4,544,545 | 10/1985 | Ryan et al. | 424/1.1 |
| 4,551,288 | 11/1985 | Kelly | 264/4.6 |
| 4,610,868 | 9/1986 | Fountain et al. | 424/1.1 |
| 4,666,711 | 5/1987 | Vanlerberghe et al. | 424/70 |
| 4,695,554 | 9/1987 | O'Connell et al. | 436/528 |
| 4,725,442 | 2/1988 | Haynes | 424/490 |
| 4,731,210 | 3/1988 | Weder et al. | 264/4.3 |
| 4,744,989 | 5/1988 | Payne et al. | 424/490 |
| 4,762,915 | 8/1988 | Kung et al. | 530/405 |
| 4,772,471 | 9/1988 | Vanlerberghe et al. | 424/450 |
| 4,789,633 | 12/1988 | Huang et al. | 435/240 |
| 4,832,872 | 5/1989 | Scandel | 252/547 |
| 4,855,090 | 8/1989 | Wallach | 264/4.1 |
| 4,897,308 | 1/1990 | Vanlerberghe et al. | 428/402 |
| 4,911,928 | 3/1990 | Wallach | 424/450 |
| 4,917,951 | 4/1990 | Wallach | 428/402 |
| 5,019,392 | 5/1991 | Wallach | 424/420 |
| 5,021,200 | 6/1991 | Vanlerberghe et al. | 264/4.3 |
| 5,032,457 | 7/1991 | Wallach | 428/402 |
| 5,260,065 | 11/1993 | Mathur | 424/450 |

FOREIGN PATENT DOCUMENTS

| | | |
|---|---|---|
| 1539625 | 1/1979 | United Kingdom . |
| 2078543 | 1/1982 | United Kingdom . |
| 2147263 | 5/1985 | United Kingdom . |
| 2166107 | 4/1986 | United Kingdom . |
| 8706499 | 5/1987 | WIPO . |

OTHER PUBLICATIONS

Murahami et al., J. Org. Chem. 47:2137–2144 (1982).
Gregoriadis, N. E. J. Med. 13:704–710 (1976).
Bangham et al. J. Mol. Biol. 13:238–252 (1965).
Szoha et al., Proc. Nat'l. Acad Sci. USA 75:4194–4198 (1978).
Baillie et al., J. Pharm. Pharmacol. 37:863–868 (1985).
Puisieux et al., "Problemes Technologiques Poses Par L'utilisation des Liposomes . . ." (1985) (no translation).
Baille et al., J. Pharm. Pharmacol 38:502–505 (1986).
Dousset et al., "Methods de Preparation des Liposomes . . ." (1985) (no translation).
Ribier et al., Colloids and Surfaces 10:155–161 (1984).
Handjani-Villa, "Les Niosomes" (1985) (no translation).
McCuthcheon, "Detergents and Emulsifiers", No. American Edition (1973).
Gregoriadis, G., Liposome Technology 2nd Ed. vol. 7, Chp. 9 (1993) 141–155.

*Primary Examiner*—Gollamudi S. Kishore

[57] ABSTRACT

Disclosed are lipid vesicles containing a blend of amphiphiles, including propylene glycol stearate, in the lipid bilayers. The vesicles may have either an aqueous or oil-filled central cavity and are particularly useful for delivering dermatological, cosmetic and pharmaceutical formulations. A method of manufacture for these vesicles is also disclosed.

8 Claims, No Drawings

PROPYLENE GLYCOL STEARATE VESICLES

This application is continuation-in-part of the U.S. Pat. application Ser. No. 07/761,253 filed on Sep. 17, 1991 now U.S. Pat. No. 5,260,065.

BACKGROUND OF THE INVENTION

The present invention relates to formulations for lipid vesicles and methods of their manufacture. More particularly, the present invention discloses paucimellar lipid vesicles designed of materials which have exceptional properties for cosmetic, edible, dermatological, and pharmaceutical use. The paucimellar vesicles have 2–10 lipid bilayers surrounding a large amorphous central cavity which can contain a water-immiscible oily material or an aqueous solution. These lipid vesicles have a combination of propylene glycol stearate and at least one other compatible amphiphile as the primary structural material of their lipid bilayers.

Lipid vesicles are substantially spherical structures made of amphiphiles, e.g., surfactants or phospholipids. The lipids of these spherical vesicles are generally organized in the form of lipid bilayers, e.g., multiple onion-like shells of lipid bilayers which encompass an aqueous volume between the bilayers. Paucilamellar lipid vesicles have 2–10 peripheral bilayers which surround a large, unstructured central cavity.

Until recently, liposome technology has been concerned mostly with vesicles composed of phospholipids. This is primarily because phospholipids are the principal structural components of natural membranes and, accordingly, lipid vesicles have been used as a model system for studying natural membranes. However, there are a number of problems associated with using phospholipids as synthetic membranes. Biological membranes are stabilized by membrane proteins and maintained by extensive enzymatic "support" systems that rapidly turn over, exchange or modify membrane lipids. Neither membrane proteins nor the requisite enzymatic support systems can be practically incorporated into the wall structure of liposomes, making the structures inherently less stable than natural membranes. In addition, the biological environment contains several potent phospholipases that rapidly break down free phospholipids. These phospholipids will attack liposomes and degrade the membrane. For these reasons, phospholipid liposomes placed in an in vivo environment are rapidly degraded.

Moreover, phospholipid liposome technology has other problems. Phospholipids are labile and expensive to purify or synthesize. In addition, classic phospholipid liposomes are in the form of multilamellar as opposed to paucilamellar vesicles and have poor carrying capacities, especially for lipophilic materials, and have poor shelf lives unless lyophilized in the dark with antioxidants. Finally, phospholipids degrade too rapidly in vivo for most pharmaceutical or vaccine applications.

For these reasons, there is increasing interest in liposomes made of commercially available nonphospholipid amphiphiles (see, e.g., U.S. Pat. No. 4,217,344, U.S Pat. No. 4,917,951, and U.S. Pat. No. 4,911,928). These molecules have a hydrophilic head group attached to a hydrophobic "tail" and are derived from long chain fatty acids, long chain alcohol's and their derivatives, long chain amines, and polyol sphingo- and glycerolipids. Commercially available amphiphile surfactants include, for example, the BRIJ family of polyoxyethylene fatty ethers, the SPAN sorbitan fatty acid esters, and the TWEEN polyoxyehtylene derivatives of sorbitan fatty acid esters, all available from ICI Americas, Inc. of Wilmington, Del. Paucilamellar vesicles comprised of such amphiphiles provide a high carrying capacity for water-soluble and water immiscible substances. The high capacity for water immiscible substances represents a unique advantage over classical phospholipid multilamellar liposomes.

Many cosmetic and dermatological preparations commonly include amphiphiles such as propylene glycol stearate, stearyl alcohol, polyoxyethylene fatty ethers (i.e., POE 10 stearyl alcohol), sorbitan fatty acid esters, and polyoxyethylene derivatives of sorbitan fatty acid esters (i.e., POE 20 sorbitan monostearate). These additives can be used as emulsifiers or thickeners, providing the "feel" to certain cosmetics and/or dermatologicals. Many of these additives also fall under the GRAS list of edible materials, and those that do not fall under the GRAS list are still likely to be non-toxic and ingestible. These additives can therefore be used in many food and pharmaceutical products. Consequently, it would be advantageous to use these additives as the lipid vesicle formers.

Accordingly, an object of the present invention is to provide a method of making paucimellar lipid vesicles using as a primary structural lipids of the bilayers amphiphiles which are commonly used in cosmetics, dermatologicals and pharmaceuticals.

Another object of the invention is to provide paucilamellar lipid vesicles which contain propylene glycol stearate and at least one other amphiphile as the structural lipids of the bilayers.

A further object of the invention is to provide a method of producing paucimellar lipid vesicles which readily encapsulate water immiscible oily materials and are manufactured from relatively inexpensive materials.

These and other objects and features of the invention will be apparent from the following description and the claims.

SUMMARY OF THE INVENTION

The present invention features lipid vesicles and a method of their manufacture using a blend of propylene glycol stearate and at least one other amphiphile as the major lipid components of the bilayers. These blended vesicles feature materials with special usefulness for cosmetic and dermatological processes and products.

The vesicles in the invention have about two-ten bilayers arranged in the form of substantially spherical shells separated by aqueous layers surrounding a large amorphous central cavity free of lipid bilayers. The lipid bilayers have as their primary lipid components a mixture of propylene glycol stearate and at least one other amphiphile selected from the group consisting of fatty alcohols, quaternary dimethyldiacyl amines, polyoxyethylene acyl alcohols, polyglycerols, sorbitan fatty acid esters, ethoxylated sorbitan fatty acid esters, fatty acids and their salts, and mixtures thereof. In particular, propylene glycol stearate is mixed with stearyl alcohol, polyoxyethylene fatty alcohols, polyoxyethylene derivatives of sorbitan fatty acid esters having 10–20 oxyethylene groups, and mixtures thereof; wherein the fatty alcohol or fatty acid groups of the polyoxyethylene fatty alcohols and the polyoxyethylene derivatives of sorbitan fatty acid esters are selected from the group consisting of radicals of palmetic acid, stearic acid, lauric acid, and oleic acid, and mixtures thereof. This mixture may further contain at least one sterol selected from the group consisting of cholesterol, cholesterol derivatives, hydrocortisone, phytosterol, and mixtures thereof, a charge producing agent, and any lipid soluble materials to be incorporated into the vesicles.

The vesicles of the invention have a central cavity carrying either water soluble materials or a water-immiscible oily solution. The basic requirement for this water-immiscible oily solution is that it is made of materials which are both water immiscible and immiscible in the lipids used to form the bilayers. Examples of these water-immiscible oily materials include mineral oils, soybean oil, paraffin waxes, petrolatum, triglyceride oils and fats, perfumes and fragrances, flavor oils, perfluorocarbon liquids, water insoluble vitamins, and a variety of water-immiscible solvents. Of particular interest is the encapsulation of anthralin or retinoic acid as the water-immiscible material. These materials provide pharmacological or dermatological benefits in addition to the benefits caused by the use of the particular lipids which form the bilayers.

The invention further features a method of producing the lipid vesicles of the invention. Oil filled vesicles, e.g., vesicles having their amorphous central cavities filled with a water-immiscible oily solution, may be formed using either the "hot loading" technique disclosed in U.S. Pat. No. 4,911,928 or the "cold loading" technique described in the U.S. Pat. No. 5,160,669, the disclosures of which are incorporated herein by reference. In either case, a lipid phase is formed by blending propylene glycol stearate and the compatible amphiphile(s), along with any sterols or lipophilic materials to be incorporated into the lipid bilayers, to form a homogenous lipid phase. In the "hot loading" technique, any water-immiscible oily material to be encapsulated in the vesicles is blended in the already formed lipid phase, forming a lipophilic phase. If any oil-soluble or oil-suspendable materials are to be encapsulated within the vesicles, they are first dispersed in the oil. The term "dispersed" as used herein includes dissolution or forming a suspension or colloid to yield a flowable phase.

Once a lipophilic phase is made, it is blended with an aqueous phase (e.g., water, saline, or any other aqueous solution which will be used to hydrate the lipids) under shear mixing conditions to form the vesicles. "Shear mixing conditions", as used herein, means a shear equivalent to a relative flow of 5-50 m/s through a 1 mm orifice.

In the "cold loading" technique, the lipid phase and the aqueous phase are blended under shear mixing conditions to form vesicles. These vesicles are then blended under low shear conditions, as described in the aforementioned U.S. Pat. No. 5,160,669.

All of the materials used to form the vesicles of the invention can also be used in the methods of the invention. Other modifications of the methods and products will be apparent from the following description and the claims.

DETAILED DESCRIPTION OF THE INVENTION

The present invention uses a blend of amphiphiles to form paucilamellar lipid vesicles. In particular, propylene glycol stearate is blended with at least one other amphiphile to form a lipid phase which can be hydrated to form vesicles. Other additives, such as a sterol, may also be blended with the lipid phase.

The preferred second amphiphiles to be used in the lipid phase are stearyl alcohol, polyoxyethylene fatty alcohols, polyoxyethylene derivatives of sorbitan fatty acid esters having 10-20 oxyethylene groups, and mixtures thereof; wherein the fatty alcohol or fatty acid groups of the polyoxyethylene fatty alcohols and the polyoxyethylene derivatives of sorbitan fatty acid esters are selected from the group consisting of radicals of palmetic acid, stearic acid, lauric acid, and oleic acid, and mixtures thereof. In a preferred embodiment of the invention, the lipid mixture of the invention contains propylene glycol stearate, stearyl alcohol and polyoxyethylene 20 sorbitan monostearate (Polysorbate 60). This mixture may further contain at least one sterol selected from the group consisting of cholesterol, cholesterol derivatives, hydrocortisone, phytosterol, and mixtures thereof, and any other materials to be incorporated into the bilayers.

The lipid vesicles of the invention are paucilamellar lipid vesicles characterized by two to ten lipid bilayers or shells with small aqueous volumes separating each substantially spherical lipid shell. The innermost lipid bilayer surrounds a large, substantially amorphous central cavity which may be filled with either an aqueous solution or a water-immiscible oily solution.

Examples of water-immiscible oily materials which can be encapsulated in the central cavity are mineral oils, soybean oil, paraffin waxes, petrolatum, triglyceride oils and fats, perfumes and fragrances, flavor oils, perfluorocarbon liquids, anthralin, retinoic acid, water insoluble vitamins, and water immiscible solvents. Avocado oil unsaponifiables can also be encapsulated in the central cavity and are particularly useful as they may additionally be used as a source of phytosterol to stabilize the vesicle bilayer.

The following Examples will clearly illustrate the efficacy of the invention.

EXAMPLE 1

In this Example, propylene glycol stearate was blended with other amphiphiles, in differing amounts, and cholesterol to obtain a formulation for aqueous filled vesicles.

TABLE 1

| Amphiphile (grams) | Sample | | | | | |
| --- | --- | --- | --- | --- | --- | --- |
|  | A | B | C | D | E | F |
| Propylene Glycol Stearate | 3.25 | 2.75 | 2.25 | 2.75 | 2.25 | 1.75 |
| Stearyl Alcohol | 0.5 | 1.0 | 1.5 | 0.5 | 1.0 | 1.5 |
| Polysorbate 60 |  |  |  | 0.5 | 0.5 | 0.5 |
| Cholesterol | 1.25 | 1.25 | 1.25 | 1.25 | 1.25 | 1.25 |

For each sample, the vesicles were made by blending the amphiphiles and the cholesterol at approximately 85° C. and then hydrating the formed lipid phase with 30 ml of water at 72° C. Hydration to form lipid vesicles was achieved by shear mixing the lipid and aqueous phases using two 60 cc syringes, connected by a stopcock. The lipid and aqueous phases were blended from one syringe to the other, forming aqueous filled vesicles in two minutes or less. However, in this and the following Examples, any method of achieving the proper shear could be used. Preferably, a flow device such as the NovaMix TM vesicle former is used. The basic details of the NovaMix TM system are described in U.S. Pat. No. 4,895,452, the disclosure of which is incorporated herein by reference.

Samples A, B and C shown on Table 1 are blends of propylene glycol stearate (PGS), stearyl alcohol (SA) and cholesterol, with decreasing ratios of PGS:SA. Microscopic examination of the resulting vesicles showed that samples A and B formed a mixture of good vesicles with maltese cross patterns visible, indicating concentric lipid bilayers, and a small population of poor, irregular vesicles which displayed tails. Sample C produced very poor vesicles.

Samples D, E and F also contained PGS, SA and cholesterol, but further contained 0.5 grams of polyoxyethylene 20 sorbitan monostearate (Polysorbate 60). The addition of Polysorbate 60 improved the shape and homogeneity of the resulting vesicles so that maltese crosses and no tails were observed. The resulting mixture was also a smoother textured product. After centrifugation of all the samples at 3500 rpm for 15 minutes, only sample E showed some separation, probably due to an excess of water.

This Example shows that paucilamellar lipid vesicles can be formed using a blend of propylene glycol stearate and at least one other amphiphile, preferably stearyl alcohol ranging from 12.5–22.0 molar percentage, and Polysorbate 60 ranging from 1.8–3.2 molar percentage, to form the lipid bilayers.

EXAMPLE 2

In this Example, lipid vesicles using the same bilayer materials as those used in Example 1 were hot loaded with soybean oil to form oil-filled paucilamellar vesicles.

TABLE 2

| Composition (grams) | Sample | | | | | |
|---|---|---|---|---|---|---|
| | A | B | C | D | E | F |
| Propylene Glycol Stearate | 2.75 | 2.75 | 2.5 | 2.5 | 2.5 | 2.5 |
| Stearyl Alcohol | 0.75 | 0.75 | 0.75 | 0.75 | 0.75 | 0.75 |
| Polysorbate 60 | | | 0.5 | 0.5 | 0.35 | 0.35 |
| Cholesterol | 1.5 | 1.5 | 1.25 | 1.25 | 1.25 | 1.25 |
| Soybean Oil | | 1.75 | | 1.75 | | 1.75 |
| Water | 30 | 28.2 | 30 | 28.2 | 30.2 | 28.5 |

For samples A, C and E, aqueous-filled lipid vesicles were formed using the syringe method described in Example 1.

For samples B, D and F, oil-filled vesicles were formed using the hot loading technique described in U.S. Pat. No. 4,911,928, the disclosure of which is incorporated herein by reference. Briefly, the vesicles were hot loaded by heating the soybean oil to 85° C., blending the soybean oil with the lipid phase (formed by mixing propylene glycol stearate, stearyl alcohol, cholesterol and, optionally, polyoxyethylene 20 sorbitan monostearate (Polysorbate 60), and then the combined lipid/oily phase was hydrated by the aqueous phase using the syringe method described in Example 1. Either hot loading or cold loading techniques may be used for soybean oil.

Samples A-F were designed to titrate the amount of Polysorbate 60 incorporated into the lipid bilayers of the vesicles. In samples A and B, aqueous-filled and oil-filled vesicles were formed without any Polysorbate 60. In samples C and D, the same aqueous-filled and oil-filled vesicles were formed using 0.5 grams of Polysorbate 60. In samples E and F, the same aqueous-filled and oil-filled vesicles were formed using 0.35 grams of Polysorbate 60.

After processing to form lipid vesicles, samples A and B, which contained propylene glycol stearate, stearyl alcohol and cholesterol, with no Polysorbate 60, had a very thick, virtually solid consistency. These samples were not examined further.

In contrast to samples A and B, samples C and D which contained the same materials as A and B, except for the addition of Polysorbate 60, had a very smooth, lotion-like consistency after processing to form lipid vesicles. Sample D, which contained vesicles encapsulating soybean oil, had a slightly smoother consistency than sample C, which contained aqueous-filled vesicles. Furthermore, while microscopic examination of samples D and C showed that both contained nice spherical vesicles with maltese crosses, indicating multiple bilayers, the oil-filled vesicles of sample D were smaller, had a narrower particle size distribution and exhibited better stability than the aqueous-filled vesicles of sample C.

Samples E and F contained the same ingredients as samples C and D respectively, except that the amount of Polysorbate 60 was titrated downward from 0.5 grams to 0.35 grams. The consistency of the samples after processing was the same as for samples C and D. However, the size and shape of the vesicles of sample E and particularly sample F were better than those of samples C and D. The mean particle diameter of the vesicles of mixtures E and F, measured by Coulter Counter (Coulter Counter Electronics Corp., Miami, Fla.), was approximately 1920 nm and 1340 nm respectively. None of the samples (B, C, D, E or F) showed any separation after centrifugation at 3500 rpm for 15 minutes.

This Example shows that the addition of Polysorbate 60, preferably ranging from 1.8–3.2 molar percentage, to form the lipid bilayers improves the consistency of the formulations of the present invention, as well as the size and shape of the lipid vesicles.

EXAMPLE 3

In this Example, the amount of stearyl alcohol and soybean oil was titrated in the formation of oil-filled vesicles, using the same materials as in Example 2.

TABLE 3

| Composition (grams) | Sample | | | |
|---|---|---|---|---|
| | A | B | C | D |
| Propylene Glycol Stearate | 2.5 | 2.5 | 2.5 | 2.5 |
| Stearyl Alcohol | 0.5 | 0.5 | 0.75 | 0.75 |
| Polysorbate 60 | 0.35 | 0.35 | 0.35 | 0.5 |
| Cholesterol | 1.25 | 1.25 | 1.25 | 1.25 |
| Soybean Oil | 1.75 | 7.0 | 7.0 | 7.0 |
| Water | 28.7 | 23.5 | 23.2 | 23.0 |

The lipid vesicles of samples A-D were hot-loaded with soybean oil using the method described in Example 2. The soybean oil could have been cold loaded as well.

Samples A-D were designed to titrate the amount of stearyl alcohol incorporated into the lipid walls, as well as the amount of soybean oil encapsulated by the vesicles. Samples A and B both contained 0.5 grams of stearyl alcohol while the amount of soybean oil was increased from 1.75 grams (5%) (sample A) to 7.0 grams (20%) (sample B).

After processing to form lipid vesicles, both samples had a smooth, cream-like consistency. Upon microscopic examination, both samples also exhibited nice looking small vesicles, the vesicles of mixture A being the most homogenous in size and shape. Sample A also exhibited maltese crosses, indicating multiple concentric bilayers. Sample B did not exhibit any maltese crosses, probably due to the greater amount of oil filling the central cavity which displaces a number of the bilayers. The mean diameters of the vesicles of samples A and B were 835 nm and 549 nm, respectively. No separation occurred in either sample after centrifugation at 3500 rpm for 15 minutes Samples C and D both contained the same amount of soybean oil as sample B, 7.0 grams (20 percent by weight of total volume), while the amount of stearyl alcohol was titrated upward from 0.5 grams to 0.75 grams.

After processing to form lipid vesicles, both samples had the same smooth consistency as samples A and B, although sample D was slightly more fluid than samples A-C, probably due to the greater amount of Polysorbate 60. Upon microscopic examination, the size and shape of the vesicles of samples C and D were good, but not quite as homogenous as the vesicles of samples A and B. Neither sample C nor sample D exhibited maltese crosses due to the greater amount of oil contained in the central cavity of the vesicles, but both samples showed birefringence. The mean diameters of the vesicles of samples C and D were 760 nm and 563 nm respectively. No separation occurred in either sample after centrifugation at 3500 rpm for 15 minutes.

This Example shows that by titrating the amount of stearyl alcohol, preferably to a range of 12.5-22.0 molar percentage, the size and shape of the lipid vesicles of the invention is improved. This Example also shows that the lipid vesicles of the invention can encapsulate a volume of oil, ranging from 20-60 percent by weight of the lipid without significantly effecting the shape or homogeneity of the lipid vesicle.

EXAMPLE 4

In this Example, avocado oil unsaponifiables was used instead of the cholesterol and/or soybean oil in the oil-filled vesicles of Examples 2 and 3.

TABLE 4

| Composition (grams) | Sample | | | |
|---|---|---|---|---|
| | A | B | C | D |
| Propylene Glycol Stearate | 1.75 | 2.5 | 2.5 | 2.5 |
| Stearyl Alcohol | 0.35 | | 0.5 | 0.5 |
| Polysorbate 60 | 0.25 | | | 0.35 |
| Cholesterol | | | | 0.5 |
| Avocado Oil Unsaponifiables | 4.0 | 2.5 | 2.5 | 2.5 |
| Water | 28.6 | 30 | 30 | 29 |

* 1 gram Avocado oil unsaponifiables contains about 0.3 grams phytosterol

The oil-filled vesicles of samples A-D were hot loaded as described in Example 2. These samples were designed to form lipid vesicles using avocado oil unsaponifiables, with and without additional cholesterol, as a component of the lipid bilayers, as well as an oily material to fill the central cavity of the vesicles.

After processing to form lipid vesicles, sample B had a cottage cheese-like consistency, while sample C had only partially hydrated lipid and clear water. These samples were not examined further.

After processing to form lipid vesicles, samples A and D had a smooth, lotion-like consistency. Microscopic examination of these samples showed nice, small, spherical vesicles with maltese crosses, indicating multiples concentric lipid bilayers. The mean diameters of these vesicles measured 1460 nm and 913 nm respectively. When centrifuged at 3500 rpm for 30 minutes, samples A and D both showed some separation, probably due to an excess of water. Sample A, which contained 4.0 grams of avocado oil with no additional cholesterol, contained a slightly better, more homogenous population of vesicles than did sample D, which contained cholesterol and only 2.5 grams of avocado oil unsaponifiables.

This Example shows that avocado oil unsaponifiables, preferably ranging from 20-65 percent by weight of the lipid, can be used along with or, more preferably, instead of cholesterol and/or soybean oil in the formation of oil-filled lipid vesicles. Avocado oil unsaponifiables provide the advantage of acting both as a source of phytosterol in the lipid bilayers, as well as a water-immiscible oily material filling the central cavity of the vesicles of the invention.

The foregoing Examples are merely illustrative and those skilled in the art may be able to determine other materials and methods which accomplish the same results. Such other materials and methods are included within the following claims.

What is claimed is:

1. A paucilamellar lipid vesicle having 2-10 bilayers surrounding an amorphous central cavity, each of said bilayers comprising a mixture of propylene glycol stearate and at least one other amphiphile selected from the group consisting of stearyl alcohol, polyoxyethylene fatty alcohols, and polyoxyethylene derivatives of sorbitan fatty acid esters having 10-20 oxyethylene groups, wherein the fatty alcohol portion of said polyoxyethylene fatty alcohol is derived from an alcohol selected from the group consisting of palmityl alcohol, stearyl alcohol, lauryl alcohol, and oleyl alcohol, and mixtures thereof, and wherein the fatty acid portion of said polyoxyethylene derivatives of sorbitan fatty acid esters is selected from the group consisting of palmitic acid stearic acid lauric acid, and oleic acid, and mixtures thereof.

2. The lipid vesicle of claim 1 wherein said other amphiphile comprises polyoxyethylene 20 sorbitan monostearate.

3. The lipid vesicle of claim 2 wherein said other amphiphile comprises stearyl alcohol.

4. The lipid vesicle of claim 1 wherein said other amphiphile comprises polyoxyethylene 10 stearyl alcohol.

5. The lipid vesicle of claim 1 wherein said mixture further comprises at least one sterol selected from the group consisting of cholesterol, hydrocortisone, phytosterol, and mixtures thereof.

6. The lipid vesicle of claim 1 wherein said paucilamellar lipid vesicle comprises an amorphous central cavity containing a water immiscible material.

7. (Amended) The lipid vesicle claim 6 wherein said water immiscible oily material is selected from the group consisting of mineral oils, soybean oil, paraffin waxes, petrolatum, triglyceride oils, fragrances flavor oils. perfluorocarbon liquids, anthralin, retinoic acid, water insoluble vitamins and mixtures thereof.

8. The lipid vesicle of claim 5 wherein said phytosterol is provided from avocado oil unsaponifiables.

* * * * *

UNITED STATES PATENT AND TRADEMARK OFFICE
CERTIFICATE OF CORRECTION

PATENT NO. : 5,439,967
DATED : August 8, 1995
INVENTOR(S) : Rajiv Mathur

It is certified that error appears in the above-indentified patent and that said Letters Patent is hereby corrected as shown below:

Column 1, line 48, replace "in vivo" with --_in vivo_--.

Column 1, line 57, replace "in vivo" with --_in vivo_--.

Column 3, line 33, replace "steroIs" with --sterols--.

Column 8, line 29, replace "amphiphilc" with --amphiphile--.

Column 8, line 39, after " acid " insert --,--.

Column 8, line 39-40, after "stearic acid" insert --,--.

Column 8, line 60, after "triglyceride oils," insert --fats, perfumes,--.

Signed and Sealed this

Sixth Day of August, 1996

*Attest:*

BRUCE LEHMAN

*Attesting Officer*     *Commissioner of Patents and Trademarks*